United States Patent [19]

Bergeron

[11] 4,017,562

[45] * Apr. 12, 1977

[54] PHOSPHONITRILATE POLYMERS AND METHOD OF PREPARATION

[75] Inventor: Charles R. Bergeron, Baton Rouge, La.

[73] Assignee: Ethyl Corporation, Richmond, Va.

[ * ] Notice: The portion of the term of this patent subsequent to Mar. 5, 1991, has been disclaimed.

[22] Filed: Dec. 14, 1973

[21] Appl. No.: 424,897

Related U.S. Application Data

[63] Continuation-in-part of Ser. No. 285,007, Aug. 30, 1972, Pat. No. 3,795,526.

[52] U.S. Cl. .............................. 260/927 N; 260/973
[51] Int. Cl.$^2$ .......................................... C07F 9/24
[58] Field of Search ....................... 260/927 N, 973

[56] References Cited

UNITED STATES PATENTS

| | | |
|---|---|---|
| 2,876,247 | 3/1959 | Rätz et al. ..................... 260/927 N |
| 3,627,841 | 12/1971 | Kober et al. ................... 260/927 N |
| 3,795,526 | 3/1974 | Bergeron ..................... 260/927 N X |

OTHER PUBLICATIONS

Shaw et al., Chemical Reviews, vol. 62, No. 1, Feb. 1962, p. 268.

*Primary Examiner*—Richard L. Raymond
*Attorney, Agent, or Firm*—Donald L. Johnson; John F. Sieberth; James M. Pelton

[57] ABSTRACT

Improved fire retardant phosphonitrilate polymer compositions are prepared by reacting a chlorophosphazene with a metal alcoholate, preferably sodium propoxide, and an alkali metal hydroxide, preferably sodium hydroxide which is first prepared by mixing alcohol and water and adding this to a dispersion of alkali metal in a solvent.

6 Claims, No Drawings

PHOSPHONITRILATE POLYMERS AND METHOD OF PREPARATION

CROSS-REFERENCE TO RELATED APPLICATION

This application is a continuation-in-part of application Ser. No. 285,007, filed Aug. 30, 1972, now U.S. Pat. No. 3,795,526.

BACKGROUND OF THE INVENTION

Phosphonitrilate polymers are known to be fire retardants for cellulosic materials: U.S. Pat. No. 3,455,713, Godfrey, Ind. Eng. Chem. Prod. Res. Develop. 9 No. 4 (1970) pgs. 426–436, South African Pat. No. 70/2767, U.S. Pat. No. 2,892,803. Such polymers are made by reacting sodium derivatives of monohydric alcohols with phosphonitrillic chlorides. Alternatively, the monohydric alcohols can be reacted with the phosphonitrillic chloride as described in Netherlands Pat. No. 71/06772.

For some processes for making flame retardant rayon, phosphonitrilates of increased viscosity are desirable. Also, greater retention of the phosphonitrilate polymer in the fiber after forming it and during laundering is desirable. The crosslinked phosphonitrilates of this invention have higher viscosity than phosphonitrilates which are not cross-linked. They also have higher phosphorus content. Other advantageous properties will be apparent from the following description of the invention.

SUMMARY OF THE INVENTION

One aspect of this invention provides a phosphonitrilate polymer composition comprising two cyclic oligomeric phosphonitrilate compounds being cross-linked by oxygen forming a P-O-P bond.

Another aspect of this invention provides a process for preparing the phosphonitrilate polymer which has two cyclic oligomeric phosphonitrilate compounds cross-linked by oxygen forming a P-O-P bond by reacting a chlorophosphazene with a metal alcoholate and from about 0.1 to about 10 percent by weight of an alkali metal hydroxide based on said alcoholate.

Another and preferred aspect of this invention is to first prepare the mixture of alcoholate and hydroxide by adding the water and alcohol in amounts to give the above portions of alcoholate and hydroxide and then adding the water-alcohol mixture to molten alkali metal dispersed in a solvent.

Another aspect of the invention provides cellulosic materials whose fire retardance is enhanced with such polymers. Such materials may be made fire retardant by the padding technique; i.e., treating the surface with the polymer or solution or suspension thereof and then drying. As a preferred embodiment of this invention, this invention provides cellulose filaments or filamentary articles having dispersed therein a flame retardant amount of such polymers. These can be made by mixing viscose and a flame retardant amount of such polymer, shaping the mixture into a filament, and coagulating and regenerating said filament.

DESCRIPTION OF PREFERRED EMBODIMENTS

Phosphazene compounds are ring or chain phosphorus-nitrogen compounds having two substituents connected to each phosphorus atom, but no substituents on nitrogen, and are characterized by a valence-unsaturated skeleton. Phosphonitrilate compounds are phosphazenes in which the substituents on the phosphorus atom are alkoxy or aryloxy radicals and have the general formula

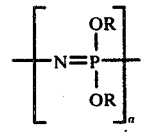

where $a$ is at least 3 and R can be the same or different alkyl or aryl radicals having up to about 6 carbon atoms.

Processes for producing phosphonitrilates result in a mixture of compounds, usually oligomers such as the cyclic trimer, tetramer, pentamer and linear polymers. According to this invention, the cyclic oligomers are cross-linked by oxygen forming a P-O-P bond. This can be illustrated by the following general formula showing two cyclic trimeric phosphonitrilates joined by a bridging oxygen atom connecting a phosphorus atom on each of the trimers.

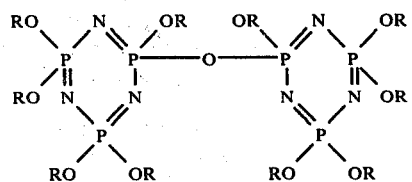

Of course three, four or more cyclic oligomers can be cross-linked in a similar manner. Not only can two or more cyclic oligomeric phosphonitrilates be cross-linked by oxygen forming a P-O-P bond, but cyclic-linear and linear-linear oligomeric cross-linking is also contemplated by this invention. One skilled in the art can envision numerous possibilities for cross-linking various cyclic and linear oligomers. Also, as when three or more oligomers are cross-linked, more than one P-O-P bond connecting a single oligomer to other oligomers is contemplated, resulting in a complex pattern of many interlocked chains and rings and mixtures thereof.

While the phosphonitrilate polymer of this invention may have mixtures of any of the above oxygen cross-linked oligomers, a preferred composition is one in which at least one of the phosphonitrilate compounds is an alkoxyphosphazene. Another preferred composition is one in which at least one of the cyclic oligomeric phosphonitrilate compounds is a cyclic trimer. Even more preferred is a composition in which at least one of the cyclic oligomeric phosphonitrilate compounds is cyclic trimeric hexaalkoxyphosphazene. Still more preferred is a composition having at least two cyclic oligomeric phosphonitrilate compounds being cross-linked by oxygen forming a P-O-P bond. A further preferred composition is one having two cyclic trimeric hexaalkoxy phosphazene compounds cross-linked by oxygen forming a P-O-P bond. Most preferred is a composition in which at least one of the cyclic oligomeric phosphonitrilate compounds is hexapropoxyphosphazene.

It has been found that the phosphonitrilate polymers of this invention can be prepared by reacting a phosphonitrilic halide, such as the chloride, with an alcohol reactant, preferably the alkali metal alcoholate, and an alkali metal hydroxide.

The nature of the phosphonitrilate polymer of this invention depends in part on the nature of the phosphonitrilic starting material. The most practical starting material is a phosphonitrilic chloride

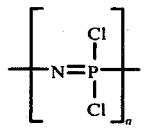

wherein $a$ is at least 3. These can be formed by any method known in the art. Exemplary methods are in Am. Chem. J. 19 782 (1897), Schenk et al, Ber. 57B 1343 (1924), U.S. Pat. Nos. 2,788,286, 2,008,799, 3,249,397, 3,347,643, 3,367,750, 3,372,005, 3,378,353, 3,379,511, 3,407,047, 3,462,247, 3,359,080, Netherlands Pat. No. 70/05128, and J. Chem. Soc. (A), pgs. 768–772 (1971).

The alcohol reactant includes both the alcohol itself and the alkali metal alcoholate derivative, the latter being preferred. Monohydric aliphatic and aromatic alcohols can be used. Of the monohydric aliphatic alcohols, those having up to six carbons are preferred. However, those having 7, 8 or more carbons can be used if desired. Of the monohydric alcohols, exemplary preferred species are methanol, ethanol, isopropanol, n-propanol, n-butanol, neopentyl alcohol, n-hexanol, 2-hexanol, mixtures thereof, and the like. Monohydric aromatic alcohols used include phenol and its substituted derivatives. For most preparations reaction of metal derivatives of the alcohols is preferred over reaction of the alcohols themselves.

Of the metals, the alkali metals are preferred. Sodium and potassium are highly preferred because of their availability, and sodium is most preferred because of its reactivity and relative inexpensiveness. The metal derivative is prepared by reacting the metal with a hydroxy compound in any convenient manner. For example, sodium can be reacted with an alcohol using an inert hydrocarbon such as benzene or heptane as a reaction medium. The sodium may be in the solid state or may preferably be melted by heating to about 110° C. When using molten sodium, it is convenient to employ a reaction medium which has a boiling point above the solidification temperature of the sodium. Toluene, kerosene, or No. 9 oil can be employed. Kerosene or No. 9 oil may be somewhat difficult to remove from the product, and accordingly, toluene is a reaction medium of choice.

It is convenient to use an excess of a hydroxy compound as a precaution against unreacted sodium. Good results are obtained utilizing a 1–10 weight percent excess. However, greater or lesser excesses can be used. If the reaction is conducted utilizing a molten metal, then it is convenient to add the hydroxy compound at a rate in which the heat of reaction will keep the metal molten. Toward the end, the reaction is slower and stirring and heating can be efficaciously employed. The reaction is continued until hydrogen evolution is complete and essentially no metal remains.

The alkali metal hydroxide is preferably sodium or potassium hydroxide, with the sodium hydroxide being more highly preferred. Only a small amount of alkali metal hydroxide is required, depending on the desired degree of oxygen cross-linking. From about 0.1 to about 10 percent by weight based on the alcoholate is reacted with the phosphonitrilic halide (e.g., chlorophosphazene). Preferably, the alkali metal hydroxide is present at from about 2 to about 6 percent by weight based on said alcoholate.

Although the alkali metal alcoholate and hydroxide can be prepared separately and then reacted with the chlorophosphazene, a particularly preferred aspect of this invention is to prepare both at the same time by mixing water with the alcohol and adding the mixture to the molten alkali metal. This procedure provides a mixture of alkali metal alcoholate and alkali metal hydroxide which can be reacted with the chlorophosphazene.

Although the mixture of alkali metal alcoholate and alkali metal hydroxide can be prepared separately and then mixed together in a solvent, it is preferred to mix the water and alcohol and add this to the dispersion of molten alkali metal. This procedure provides an intimate and substantially uniform mixture of the alcoholate and hydroxide so that on reaction with the chlorophosphazene a more regularly cross-linked phosphonitrilate polymer product is produced. By mixing in a solvent the separately prepared alcoholate and hydroxide, the dispersion formed is not as uniform and may contain lumps of either the solid alcoholate or hydroxide. Without limiting the invention, it is believed that a less uniform dispersion would produce a more localized cross-linking in the phosphonitrilate polymer and, hence, a less desirable product. Hence, a most preferred embodiment of this invention is in a process for preparing a phosphonitrilate polymer having an average molecular weight of from about 800 to about 2000 comprising reacting at a temperature of from about 55° to 110° C for a period from about 0.5 to about 10 hours in a hot inert solvent a cyclic oligomeric chlorophosphazene having the general formula

wherein $a$ is at least 3 with from about 5 to about 15 weight percent excess of a mixture of an alkali metal alcoholate and from about 0.1 to about 10 percent by weight of an alkali metal hydroxide based on said alcoholate, the improvement comprising preparing said mixture by adding an alcohol and water to a slurry of said solvent in an alkali metal. In other words, the improved process of this invention is a process for preparing a phosphonitrilate polymer having an average molecular weight of from about 800–200 comprising adding an alcohol and water to a slurry of an alkali metal in an invert solvent, whereby a mixture of an alkali metal alcoholate and an alkali metal hydroxide in said solvent is formed and reacting said mixture with a cyclic oligomeric chlorophosphazene having the general formula

wherein $a$ is at least 3 at a temperature of from about 55° to about 110° C for a period of from about 0.5 to about 10 hours in a hot inert solvent, said mixture having from about 5 to about 15 weight percent excess of the theoretical amount alkali metal alcoholate and from about 0.1 to about 10 percent by weight of said alkali metal hydroxide based on said alcoholate.

Except for the presence of the alkali metal hydroxide, the preparation of the phosphonitrilate proceeds normally according to the methods referred to hereinabove. The reaction mixture which contains the solvent, e.g., benzene, toluene or heptane, any excess unreacted monohydric alcohol, e.g., propanol, the metal alcoholate, e.g., sodium propoxide, and the alkali metal hydroxide, e.g., sodium hydroxide, is reacted with the phosphonitrilic halide. It is preferred that the total of sodium propoxide and sodium hydroxide be in excess over the theoretical requirement, usually two molecules of alcohol for each unit of chlorophosphazene. In this instance, a total excess of sodium alcoholate and hydroxide of from about 5 to about 15 weight percent over the theoretical requirement is conveniently employed.

In many instances, the reaction is rapid and exothermic at the beginning and requires no heating. After mixture of the reactants is complete it may be convenient to heat the resultant reaction mass and hold it at reflux temperature for such time as analysis indicates complete reaction. Reaction times in the range of from one-half to 10 hours can be used. This is somewhat dependent upon the reaction temperature which is usually within the range of from ambient to 110° C; more preferably from about 55° to 110° C.

After conduction of the reaction, the excess free hydroxy compound and the solvent are removed by distillation or other suitable means. These can be recycled for later use.

As with the preparation of the metal derivative of the hydroxy compound the phosphazene synthesis proceeds well at ambient pressure. Accordingly, atmospheric pressure is of choice. However, greater of lesser pressures can be used if desired.

It is to be understood that mercaptides can be used in a fashion similar to that described above to prepare the sulfur compounds analogous to the above-described phosphazenes.

After removal of the free hydroxy compound and solvent, it is convenient to isolate the product from the resultant mass by water-washing followed by stripping the remainder of the solvent. In many instances, best results are obtained by using plurality of water washes. In many instances, two washes will suffice. For precaution against emulsions during washing, it is preferred to have the water washes conducted such that the water has a pH of 9 or higher. Water-washing is employed by mixing the phosphazene product with water and agitating. Typical agitating times are 10 to 20 minutes but shorter or longer times can be employed, if desired. If in the first water wash, a rag layer appears, it can be left with the organic layer for a subsequent wash. If emulsion appears in the second wash, sodium chloride or other salt can be added to increase the density difference between the phases.

After water-washing and separating, the organic layer can be subjected to distillation to remove solvent.

From the preceding description, a preferred embodiment of this invention is a process for preparing the phosphonitrilate polymer composition described above comprising reacting in a hot inert solvent a cyclic oligomeric chlorophosphazene with a metal alcoholate and from about 0.1 to about 10 percent by weight of an alkali metal hydroxide based on said alcoholate. In a more highly preferred embodiment, said reacting is characterized by the slow addition of said metal alcoholate and said alkali metal hydroxide to said chlorophosphazene. Slow addition is preferred to allow the smaller amount of alkali metal hydroxide to form the P-O-P bonds cross-linking the phosphonitrilate polymer. By slow addition is meant addition over a period covering from about 10 to about 30 percent of the total reaction time.

EXAMPLE I

A mixture of sodium propoxide and sodium hydroxide was made by adding 500 parts of heptane and 49 parts of sodium to a clean, dry reaction vessel. The reaction vessel was heated at atmospheric pressure and with agitation to about 100° C. The sodium melted, forming a dispersion in the heptane. To this dispersion was added dropwise 114 parts of n-propanol and 3.5 parts of water forming a slurry of sodium propoxide and sodium hydroxide in heptane.

In another clean, dry reaction vessel, after flushing with nitrogen, was added 116 parts of chlorophosphazene $(PNCl_3)_x$, where $x = 3.7$, dissolved in 126 parts of monochlorobenzene. This solution was heated to about 95° C and then the sodium hydroxide-sodium propoxide mixture prepared above was added over a period of 1.25 hours. The reaction mass was heated at about 97° C for an additional period of 4 hours.

The reaction mass was then cooled, washed with about 550 parts of water, the water phase was separated and the organic phase dried. While drying, a large amount of sodium chloride precipitated from the organic phase. The organic phase was filtered and dried again. About 116 parts of product was recovered. The product was analyzed with the following result:

Phosphorus = 20.1 weight percent
Nitrogen = 9 weight percent
Average Molecular Weight = 957
Viscosity = 4592 centipoise
Inorganic chloride = 0.09 weight percent
Total chloride = 2.41 weight percent The analysis indicates the product was cross-linked with P-O-P bonds. In contrast, phosphonitrilate polymer prepared without sodium hydroxide according to the above procedure, has a molecular weight of about 600, viscosity of about 80 centipoise and phosphorus content of about 19 weight percent. If the product has been pure oxygen cross-linked cyclic trimeric hexapropoxy-phosphazene, the molecular weight should be about 1080.

Similar results can be obtained when the propanol is replaced with methanol, ethanol, n-butanol, hexanol, phenol, mixtures thereof, and the like.

Similar materials are obtained when from about 0.1 to about 10 weight percent sodium hydroxide is used. Cross-linked phosphonitrilate polymers having the following characteristics are within the scope of this invention:

Viscosity = 1000–50,000 centipoise
Phosphorus = 20–26 weight percent
Average Molecular Weight = 800–2000

A preferred cross-linked phosphonitrilate composition of this invention has the following analysis:

Viscosity = 15,000 centipoise

Phosphorus = 22 weight percent
Residual Chloride = 0.5 weight percent
Residual Solvent = 0.5 weight percent
Acid NO. = 0.1
Average Molecular Weight = about 1200
Color Gardner = 8

Phosphonitrilate polymers prepared by the process of this invention can be used as flame retardant agents. For example, the above products can be used as a flame retardant in polyester. In addition, those compounds are very useful as fire retardants for cellulose materials, including fibers, filaments, and fabrics.

These materials may be applied to the cellulose by dipping, spraying, or other means utilized for treating the surface. Alternatively, for rayon and other regenerated cellulosics, one or more of the materials may be impregnated or added to the product by incorporation in the viscose prior to spinning. The amount of phosphonitrilic polymer flame retardant dispersed in the regenerated cellulose will vary from about 1 to about 30 weight percent and preferably from about 2 to about 20 weight percent based on the weight of the filament.

For impregnation prior to spinning and the finished materials, one may proceed according to the teachings of Godfrey U.S. Pat. No. 3,455,713. That patent is incorporated by reference herein as if fully set forth. Accordingly, one method of preparing cellulose filaments and filamentary articles according to this invention is to use the flame retardants provided herein according to the method set forth in Godfrey supra. Likewise, the instant invention provides regenerated cellulose filaments and filamentary articles prepared from the flame retardants, herein provided as incorporated utilizing the techniques set forth by Godfrey.

This invention can be extended to preparation and use of materials made by the above procedures where the alkanols or polyols are substituted by halogen, e.g. chlorine and bromine. Suitable monohydric alcohols for this embodiment are made from epichloro- or epibromohydrin. Likewise, 2,3-dichloropropanol, and 2,3-dibromopropanol are suitable.

Likewise, this invention can be extended to preparation and use of materials made by the above procedure where a monohydroxy phenol is substituted for all or part of the monohydric alcohol. Phenol itself is preferred as are the brominated phenols.

What is claimed is:

1. A process for preparing a phosphonitrilate polymer having an average molecular weight of from about 800 to about 2000 comprising adding an alcohol and water to a slurry of an alkali metal in an inert solvent to form a mixture of an alkali metal alcoholate and an alkali metal hydroxide in said solvent and reacting said mixture at a temperature of from about 55° to about 110° C for a period of from about 0.5 to about 10 hours in a hot inert solvent with a cyclic oligomeric chlorophosphazene having the general formula

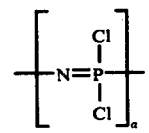

wherein $a$ is at least 3, said mixture having from about 5 to about 15 weight percent excess of the theoretical amount of said alkali metal alcoholate and from about 0.1 to about 10 percent by weight of said alkali metal hydroxide based on said alcoholate.

2. A process of claim 1 wherein said alkali metal hydroxide is present at from about 2 to about 6 percent by weight based on said alcoholate.

3. A process of claim 1 wherein said reacting is characterized by the slow addition of said metal alcoholate and said alkali metal hydroxide to said chlorophosphazene.

4. A process of claim 1 wherein the alkali metal of said alkali metal alcoholate and said alkali metal hydroxide is sodium or potassium.

5. A process of claim 1 in which said alkali metal alcoholate has up to about 6 carbon atoms.

6. A phosphonitrilate polymer produced by the process of claim 1.

* * * * *